United States Patent [19]
Gal et al.

[11] 4,169,858

[45] Oct. 2, 1979

[54] PROCESS FOR PREPARING A KETONE

[75] Inventors: George Gal, Watchung; Seemon H. Pines, Murray Hill, both of N.J.

[73] Assignee: Merck & Co., Inc., Rahway, N.J.

[21] Appl. No.: 883,759

[22] Filed: Mar. 6, 1978

Related U.S. Application Data

[63] Continuation-in-part of Ser. No. 753,151, Dec. 31, 1976, abandoned.

[51] Int. Cl.$^2$ .................. C07C 45/00; C07C 45/16
[52] U.S. Cl. ........................ 260/590 R; 260/592; 568/715
[58] Field of Search ............... 260/590 R, 592, 618; 568/715, 803

[56] References Cited

U.S. PATENT DOCUMENTS 2,983,734  5/1961  Sargent ...................... 260/618 H

OTHER PUBLICATIONS

Ruotsatainen et al., Chem. Abst., vol. 73, pp. 293, #13984F (1970).
Virtanen et al., Chem. Abst., vol. 74, p. 262, #63683B (1971).
Hickenbottom, "Reactions of Organic Compounds", pp. 143–145 (1957).
McDonald et al., J.A.C.S., vol. 85, pp. 4004–4009 (1963).
Alder et al., Acta. Chemica Scand., vol. 15, pp. 257–269 (1961).

*Primary Examiner*—James H. Reamer
*Attorney, Agent, or Firm*—Daniel T. Szura; Harry E. Westlake, Jr.

[57] ABSTRACT

A process for preparing methyl vanillyl ketone from guaiacol is disclosed.

12 Claims, No Drawings

PROCESS FOR PREPARING A KETONE

This application is a continuation in part of Ser. No. 753,151, filed Dec. 31, 1976, now abandoned.

BACKGROUND OF THE INVENTION

The present invention is concerned with a novel preparation of methyl vanillyl ketone from guaiacol.

Methyl vanillyl ketone has the formula:

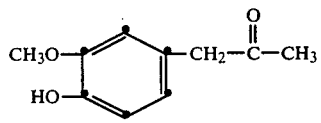  I

It is an intermediate in the preparation of the hypertensive agent, L-α-methyl-3,4-dihydroxyphenylalanine. The ketone (I) can be prepared from the substituted benzaldehyde, vanillin, or from a suitably substituted phenyl acetonitrile. These processes and/or the preparation of the hypertensive agent are disclosed in U.S. Pat. Nos. 3,344,023 and 3,366,679. Of the two known processes for preparing the ketone (I), the preferred process utilizes the vanillin starting material. Vanillin is expensive and an alternate route to the ketone (I) using a less expensive, readily available starting material has been sought.

The present process provides such a process, using guaiacol, having the formula

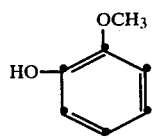

as the starting material.

SUMMARY OF THE INVENTION

A process for preparing methyl vanillyl ketone from guaiacol.

DESCRIPTION OF THE PREFERRED EMBODIMENTS

An embodiment of the present invention is a process for preparing a compound having the formula

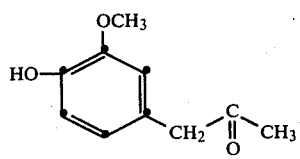  I which comprises (a) reacting a compound having the formula

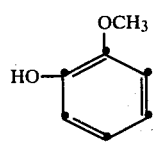  II with 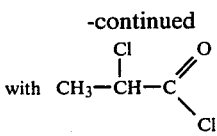

in the presence of a Friedel Crafts catalyst to obtain

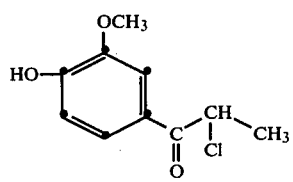  III (b) reacting a compound III with a strong base in the substantial absence of oxygen to obtain

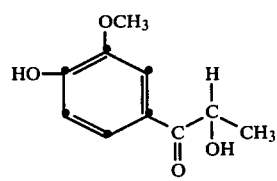  IV (c) reducing compound IV with hydrogen in the presence of a catalyst to obtain

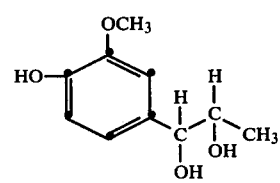  V and (d) rearranging compound V to obtain compound I.

The process is illustrated in the following sequence of equations:

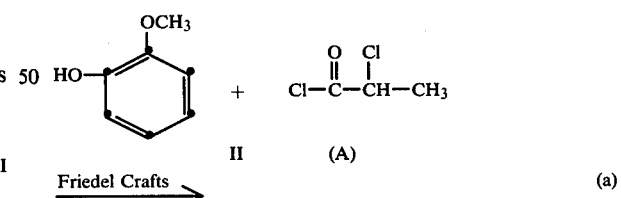  (a)

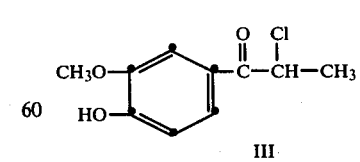

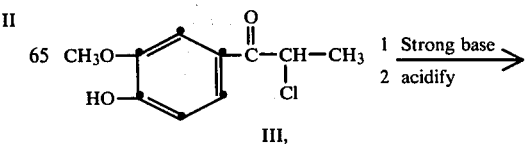

-continued

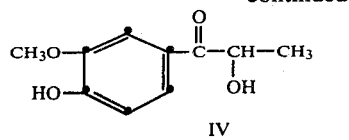
IV

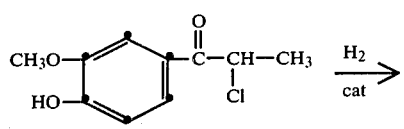
IV

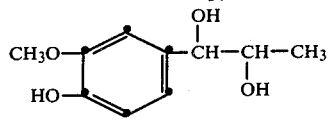
V

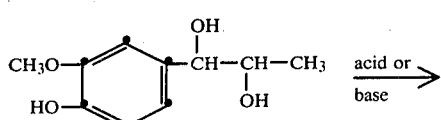
V

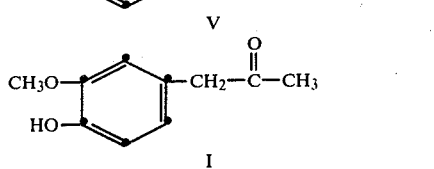
I

Step (a) is a Friedel Crafts acylation. While catalysts such as $SnCl_4$, $TiCl_4$, $ZnCl_2$, $FeCl_3$ or HF can be used, $AlCl_3$ is preferred. The acylation is most efficiently carried out when at least one mole of the catalyst ($AlCl_3$) is provided for each of the reactants, II and (A). Reaction temperatures ranging from $-10°$ C. to $50°$ C. can be used. The reaction is generally carried out in a solvent such as ethylene dichloride, nitrobenzene, carbon disulfide the like. The preparation of the bromo analog of the formula III compound is described in the Journal of the American Chemical Society 68, 1916 (1946).

In Step (b) the chloro compound III is converted to the corresponding hydroxy compound IV by treatment with an appropriate strong base. The reaction is conveniently carried out in water as the reaction medium. Any strong base, such as NaOH or KOH, may be used. The reaction temperature may be varied from $-10°$ C. to $80°$ C. A feature of this reaction with base is that it be carried out in the substantial absence of oxygen. If oxygen is not substantially excluded, the yield is reduced. After the reaction with base is complete, the reaction mixture is cooled and then is acidified with a strong acid, e.g. $H_2SO_4$, HCl, $H_3PO_4$ etc. The product IV may be isolated if desired. However, the reaction mixture containing product IV can conveniently be used directly in the next step after simply adjusting the pH to the desired level. The preparation of compound IV from the corresponding α-acetoxy derivative is reported in the Journal of the American Chemical Society 61, 2204–2206 (1939).

Step (c) embodies catalytic reduction of the IV compound. Any suitable reducing system may be utilized. A preferred system utilizes hydrogen and a heterogenous metal-containing catalyst such as Raney nickel, 60% nickel on Kieselguhr, Pt/C, Pd/C and the like. Raney nickel is a more preferred catalyst. The reduction (or hydrogenation) is carried out on the aqueous system containing the IV compound. The pH of this aqueous system is adjusted by addition of a suitable mineral acid to the pH range proper for the particular catalyst system used. In the case of the Raney nickel catalyst, the reduction is best carried out in a non-basic medium with the system initially at about pH 4.5. Beginning at a much lower pH diminishes catalyst activity. Excess by-product formation occurs if the pH rises above about 7.5 during the hydrogenation. Reaction temperature may be varied in the range of 20° C. to 200° C. with 70° C. to 90° C. being preferred. The hydrogen pressure may also be varied from atmospheric to 800 psig.

Step (d) involves a rearrangement of the Formula V compound. The rearrangement is preferably carried out in a liquid reaction medium in the presence of an acid or base. A more preferred system involves adding an aqueous solution of Formula V to a two phase mixture of aqueous acid and an immiscible solvent such as benzene, $CCl_4$, chlorobenzene, toluene and the like—and removing $H_2O$ from the system by azeotropic distillation to maintain a constant volume. Under these conditions by-product formation is minimized.

The product of the present process, namely the methyl vanillyl ketone of formula I, is used as an intermediate in the preparation of the antihypertensive agent α-methyl-3,4-dihydroxyphenyl alanine having the formula

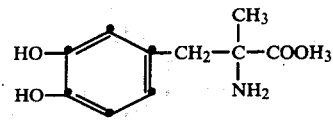

The following example illustrates the process of the present invention. Temperatures are in °C. unless otherwise indicated.

EXAMPLE 1

A. Preparation of α-Chloropropioguaiacone

To an agitated slurry of 13.8 g anhydrous aluminum chloride in 25 ml ethylenedichloride is added 6.7 g 2-chloropropionylchloride at ambient temperature. The mixture is stirred for an additional 15 minutes, then 6. g guaiacol is added dropwise under nitrogen with agitation at 15°–20° C.

The reaction mixture after aging at ambient temperature for 20 hours is quenched onto ice-water. The layers are separated and the aqueous phase is extracted with ethylenedichloride. The combined organic phase is washed with water, then the solvent is recovered in vacuo. The oily residue is recrystallized from a solvent mixture of 4 ml of ethylacetate and 20 ml cyclohexane. The crystalline α-chloropropioguaiacone m.p. 81°–83°, is filtered and washed with a cold solvent mixture of 15% ethylacetate 85% cyclohexane, and dried in vacuo.

B. Preparation of α-Hydroxypropioguaiacone

To a slurry of 11.61 g α-chloropropioguaiacone in 110 ml of oxygen free water is added 100 ml 1.5 N sodium hydroxide in an inert atmosphere. The reaction mixture is stirred at 40°–43° C. for four hours. After cooling the solution to ambient temperature, the pH is adjusted to 4.2 by adding 30% sulfuric acid. The solution is decolorized by charcoal treatment and used directly in in the next step.

If one desires, the pure α-hydroxypropioguaiacone can be crystallized by evaporation of part of the water, giving, after washing and drying, the known product, mp 109°–110°.

C. Preparation of 1-(4-Hydroxy-3-Methoxyphenyl)-Propane-1,2-diol

An aqueous solution of α-hydroxypropioguaiacone (from step B) is hydrogenated to 1-(4-hydroxy-3-methoxyphenyl)-propane-1,2-diol at 80° C. and 90 p.s.i. hydrogen over 1.0–1.2 g Raney nickel.

The mixture is cooled to room temperature after the theoretical amount of hydrogen is absorbed. The catalyst is filtered off and the aqueous solution of diol is used directly in the next step.

D. Preparation of Methylvanillyl ketone (MVK)

To a refluxing azeotropic mixture of 125 ml toluene and 100 ml 10% sulfuric acid is added an aqueous solution (~250 ml.) to 9.0 g 1-(4-hydroxy-3-methoxyphenyl)-propane-1,2-diol (from step C) at such a rate that the volume of the aqueous phase remained constant during the addition, returning the toluene and separating the aqueous phase of the distillate by a Dean-Stark head. The separation of the water is discontinued after ~250 ml is collected and the reaction mixture is refluxed for an additional hour.

After cooling the reaction mixture to room temperature the two phases are separated. The aqueous layer is extracted with toluene and the combined organic phase is washed with water and the toluene is removed in vacuo. The concentrate is 86% pure methylvanilly ketone by gc. assay and may be further purified by distillation, if desired.

The following examples demonstrate the unexpected improvement obtained when the hydrolysis of Step (b) (see page 4) is carried out in the substantial absence of oxygen.

EXAMPLE 2

Step (b) Carried Out in the Presence of Oxygen 1.07 grams of α-chloropropioguaiacone was dissolved in 10 ml of 1 N sodium hydroxide and heated to 45° C. After 6 hours, 5 ml of 1 N sodium hydroxide was added and the mixture was allowed to stand at room temperature overnight. The mixture was then added dropwise to 15 ml of 2 N HCl at 10° C. The reaction mixture was extracted with ether. The product recovered from the ether extract was α-hydroxy propioguaiacone; the yield was 51.9% (510 mg).

EXAMPLE 3

Step (b) Carried Out in the Substantial Absence of Oxygen 1130 ml of water and 111.61 g of α-chloropropioguaiacone were charged to an appropriately fitted flask. The flask was pumped with nitrogen and vacuum several times. Then, an oxygen free solution of 62.42 g of sodium hydroxide in 1000 ml of water was added to the flask with stirring. The reaction mixture was heated to 42° C. and maintained at 40°–43° C. with stirring for four hours. After cooling the mixture to 18° C., 257 ml of 30% sulfuric acid were added. 2.23 g of Charcoal (Darco G-60) were added, the mixture was stirred for 10 minutes and then it was filtered. The filter cake was washed with 15 ml of H₂O. The product obtained from the filtrate was α-hydroxypropioguaiacone, the yield was 88.4% (90.2 g).

As these examples clearly show, by carrying out the hydrolysis reaction in the substantial absence of oxygen (Example 3), the yield of product increased from 51.9% (Example 2) to 88.4% (Example 3).

Claims to the invention follow.

What is claimed is:

1. A process for preparing a compound having the formula

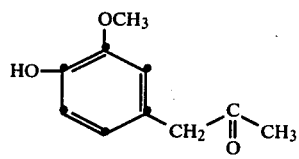

which comprises (a) reacting a compound having the formula

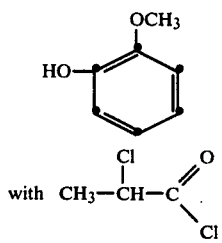

in the presence of a Friedel Crafts catalyst to obtain

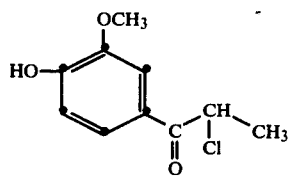

(b) reacting compound III with a strong base in the substantial absence of oxygen to obtain

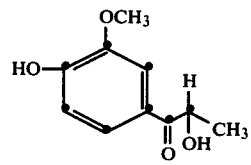

(c) reducing compound IV with hydrogen in the presence of a catalyst to obtain

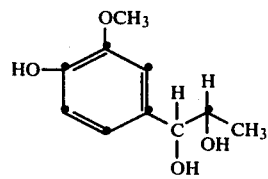

and (d) rearranging compound V to obtain compound I.

2. The process of claim 1 wherein in step (a) the Friedel Crafts catalyst is AlCl₃.

3. The process of claim 2 wherein in step (b) the strong base is NaOH or KOH.

4. The process of claim 3 wherein in step (c) the catalyst is a heterogenous, metal containing catalyst.

5. The process of claim 4 wherein said reduction is carried out in an acidic aqueous system.

6. The process of claim 5 wherein said catalyst is Raney nickel and the pH of said aqueous system is not less than about 4.5.

7. The process of claim 6 wherein in step (d) the catalytic agent is a strong mineral acid.

8. The process of claim 7 wherein said mineral acid is $H_2SO_4$.

9. The process of claim 8 wherein said compound V is added to said mineral acid.

10. The process comprising step (b) of claim 1.

11. The process of claim 10 wherein said reaction is carried out in an aqueous medium.

12. The process of claim 11 wherein said base is NaOH or KOH.

* * * * *